United States Patent [19]

Meyer et al.

[11] Patent Number: 4,518,776

[45] Date of Patent: May 21, 1985

[54] PROCESS FOR PRODUCING SULFONYLUREAS

[75] Inventors: Willy Meyer, Riehen; Werner Föry, Basel; Werner Töpfl, Dornach, all of Switzerland

[73] Assignee: Ciba Geigy Corporation, Ardsley, N.Y.

[21] Appl. No.: 511,830

[22] Filed: Jul. 8, 1983

[30] Foreign Application Priority Data

Jul. 19, 1982 [CH] Switzerland .................. 4396/82

[51] Int. Cl.³ .................. C07D 251/46; C07D 251/18; C07D 239/69; C07D 401/12
[52] U.S. Cl. .................................... 544/206; 544/207; 544/208; 544/209; 544/211; 544/212; 544/320; 544/321; 544/331; 544/332
[58] Field of Search ............... 544/197, 198, 206, 207, 544/208, 209, 211, 212, 320, 321, 331, 332

[56] References Cited

U.S. PATENT DOCUMENTS

| | | | |
|---|---|---|---|
| 4,214,890 | 7/1980 | Levitt | 544/212 |
| 4,348,219 | 9/1982 | Levitt | 544/212 |
| 4,435,205 | 3/1984 | Reap | 544/211 |
| 4,444,583 | 4/1984 | Meyer et al. | 71/93 |

FOREIGN PATENT DOCUMENTS 2078728  1/1982  United Kingdom ............... 544/212

*Primary Examiner*—John M. Ford
*Attorney, Agent, or Firm*—Karl F. Jorda

[57] ABSTRACT

There is described a process for producing sulfonylureas of the formula

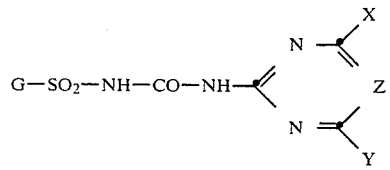

wherein

G is an unsubstituted or substituted furanyl, thienyl, pyrrolyl, pyridinyl or phenyl radical,
X is alkyl, haloalkyl, alkoxy, alkylthio, halogen, haloalkoxy, alkylamino or dialkylamino,
Y is alkyl, alkoxy or haloalkoxy,
Z is a nitrogen atom or the methyne group —CH=.

This novel process comprises reacting a sulfonamide of the formula $$G-SO_2-NH_2,$$

in the presence of a base, with a chloroformic acid ester of the formula $$Cl-CO-Q-T,$$

or a sulfonyl chloride of the formula $$G-SO_2Cl,$$

in the presence of a base, with a urethane of the formula $$H_2N-CO-Q-T;$$

and converting the formed carbamate of the formula $$G-SO_2-NH-CO-Q-T$$

by reaction with an amine of the formula

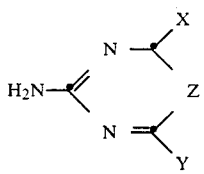

into the sulfonylurea of the above formula.
There is also described novel sulfonylcarbamates of the above formula as intermediates.

11 Claims, No Drawings

PROCESS FOR PRODUCING SULFONYLUREAS

The present invention relates to a novel process for producing sulfonylureas having a herbicidal action and an action regulating plant growth, and also to novel sulfonylcarbamates produced as intermediates.

The sulfonylureas to be produced by the novel process according to the invention are described, together with their properties, in the U.S. Pat. Nos. 4,127,405, 4,301,286 and 4,302,241, in the European Offenlegungsschriften Nos. 23422, 44807 and 44808, and also in the Swiss Patent Application Nos. 4667/81-0, 5075/81-2 and 2205/82-3.

The known processes are disadvantageous either in that isocyanate derivatives or isothiocyanate derivatives have to be reacted, the handling of which is difficult on account of the high reactivity of this class of compounds, or in that there occur during the synthesis from phenyl carbamates ecologically unfavourable byproducts, for example phenols.

It is therefore the object of the present invention to provide a process which avoids the use of compounds difficult to handle, and the occurrence of by-products which contaminate the environment.

It is hence suggested according to the invention that the herbicidal and plant-growth-regulating sulfonylureas of the general formula I

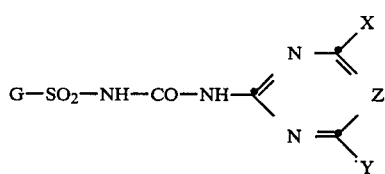

wherein
Z is an —N= or —CH= radical,
G is a radical of the formula

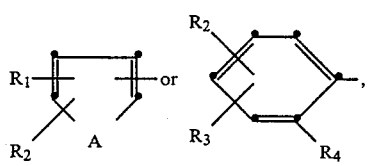

X is $C_1$–$C_4$-alkyl, $C_1$–$C_4$-haloalkyl, $C_1$–$C_4$-alkoxy, $C_1$–$C_4$-alkylthio, halogen, $C_1$–$C_4$-haloalkoxy, $C_1$–$C_4$-alkylamino or di-$C_1$–$C_4$-alkylamino,
Y is $C_1$–$C_4$-alkyl, $C_1$–$C_4$-alkoxy or $C_1$–$C_4$-haloalkoxy,
A is oxygen, sulfur, —$NR_5$— or —C≡N—, where $R_5$ is hydrogen, $C_1$–$C_4$-alkyl or —CO—$C_1$–$C_4$-alkyl,
$R_1$ is hydrogen, $C_1$–$C_4$-alkyl, halogen, nitro, cyano, —$NH_2$, —$S(O)_n$—$C_1$–$C_4$-alkyl, —$SO_2$—$C_1$–$C_4$-alkoxy, —$SO_2$—di-$C_1$–$C_4$-alkylamino, —CHO, —$CONH_2$, —D—$C_3$–$C_5$-alkynyl, —CO—D—$C_3$–$C_5$-alkynyl, —D—$C_1$–$C_4$-alkyl, —D—$C_3$–$C_5$-alkenyl, —CO—$C_1$–$C_4$-alkyl, —CO—D—$C_1$–$C_4$-alkyl or —CO—D—$C_3$–$C_5$-alkenyl, n being one or two, and D being an oxygen, sulfur, —NH— or —N($C_1$–$C_4$-alkyl)-bridge,
$R_2$ is hydrogen, halogen, $CF_3$, $NO_2$, $C_1$–$C_4$-alkyl or $C_1$–$C_4$-alkoxy,
$R_3$ is hydrogen, fluorine or chlorine, and
$R_4$ is halogen, $C_1$–$C_4$-alkyl, nitro, cyano, —$NH_2$, —$S(O)_n$—$C_1$–$C_4$-alkyl, —$SO_2$—$C_1$–$C_4$-alkoxy, —$SO_2$—di—$C_1$–$C_4$-alkylamino, —CHO, —$CONH_2$, —D—$C_3$–$C_5$-alkynyl, —CO—D—$C_3$–$C_5$-alkynyl, trifluoromethyl, or $C_1$–$C_4$-alkoxy substituted by cyano, halogen, $C_1$–$C_4$-alkoxy or $C_1$–$C_4$-alkylthio, or is —D—$C_1$–$C_4$-alkyl, —D—$C_3$–$C_5$-alkenyl, —CO—$C_1$–$C_4$-alkyl, 1,2-dichlorovinyloxy, —CO—D—$C_1$–$C_4$-alkyl or —CO—D—$C_3$–$C_5$-alkenyl, n being one or two, and D being an oxygen, sulfur, —NH— or —N($C_1$–$C_4$-alkyl)-bridge.

be produced by a process comprising reacting a sulfonamide of the formula II

in the presence of a base, with a chloroformic acid ester of the formula III

or a sulfonyl chloride of the formula IV

in the presence of a base, with a urethane of the formula V

wherein G has the meaning defined under the formula I,
Q is oxygen or sulfur, and
T is $C_1$–$C_4$-alkyl, benzyl, $C_1$–$C_4$-haloalkyl, $C_1$–$C_3$-cyanoalkyl, $C_2$–$C_5$-alkenyl, or alkoxyalkyl or alkylthioalkyl having a total of at most 5 carbon atoms; and converting the formed carbamate of the formula VI

by reaction with an amine of the formula VII

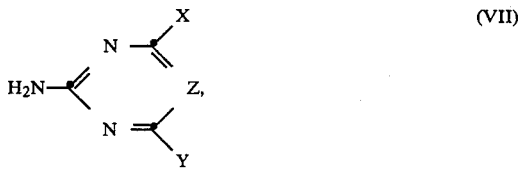

wherein G, Q, T, X, Y and Z have the meanings defined in the foregoing, into the sulfonylurea of the formula I.

By halogen is meant within the scope of the above definition in general fluorine, chlorine, bromine or iodine, fluorine and chlorine being preferred. Preferred as substituent of the radical G is particularly chlorine, and as substituent of an alkyl group, which in its turn can be part of a radical, especially fluorine.

Examples of alkyl are: methyl, ethyl, n-propyl and i-propyl or the isomeric butyl grups. Alkyl is itself to be understood as being a substituent or as part of another substituent, for example alkoxy or alkylthio. Preferred alkyl groups are in each case unbranched alkyl chains, especially however methyl and ethyl.

By alkenyl is meant as a rule: allyl, 2-butenyl, 3-butenyl, 2-isobutenyl, isopropenyl, 2-pentenyl, 3-pentenyl or 4-pentenyl, particularly allyl and 4-pentenyl.

By alkynyl is meant in general: propargyl, 2-butynyl, 3-butynyl, methylpropargyl, 2-pentynyl, 3-pentynyl and 4-pentynyl.

The heterocycles which are embraced by the definition of the radical G are: thiopene, furan, pyrrole and pyridine.

Preferred pyrimidine and triazine rings are those in which X is methyl, ethyl, fluoromethyl, trifluoromethyl, methoxy, ethoxy, i-propyloxy, methylthio, chlorine, bromine, difluoromethoxy, 2,2,2-trifluoroethoxy, methylamino or dimethylamino, and Y is methyl, methoxy or difluoromethoxy.

The reaction of the sulfonamides of the formula II with the chloroformic acid esters of the formula III can be performed in the presence of a suitable inert aprotic solvent, or in the absence of a solvent. The use of a solvent has however proved advantageous. Suitable solvents are: hydrocarbons, such as benzene, toluene and xylene; ethers, such as diethyl ether, ethylene glycol dimethyl ether, diethylene glycol dimethyl ether, tetrahydrofuran and dioxane; ketones, such as acetone, ethyl methyl ketone and cyclohexanone; nitriles, such as acetonitrile and propionitrile; and dimethyl sulfoxide. The reaction is performed in the presence of at least equimolecular amounts of a base. Suitable bases are carbonates, such as sodium and potassium carbonate, hydrogen carbonates, such as sodium and potassium hydrogen carbonates, oxides, such as calcium and magnesium oxides, and tertiary amines, such as trimethylamine, triethylamine, quinuclidine, quinoline, pyridine and tripropylamine. The base is advantageously used in excess. There are thus preferably used 1 to 5 mols of base, especially 1.1 to 1.5 mols, per mol of sulfonamide. Larger excesses of base are used in particular when the reaction is performed without solvent, and the base, preferably a liquid tertiary amine, simultaneously serves as reaction medium. The reaction temperatures are as a rule between 0° and 140° C., preferably between 10° and 80° C.

The reaction of the sulfonyl chlorides of the formula IV with the urethanes of the formula V is carried out under the same reaction conditions as those for the reaction of the compounds of the formulae II and III.

The sulfonylcarbamates of the formula VI obtained as intermediates are reacted with the amines of the formula VII by the mixture of the two reactants being heated until a cleavage of the alcohol or mercaptan has occurred. The reaction can be performed either without solvent or in the presence of an inert solvent. The reaction mixture is in general heated until the commencement of the cleavage reaction of alcohol or mercaptan, and is held at this temperature until a complete conversion is obtained. The temperature is as a rule 50° to 220° C., preferably 80° to 160° C. Solvents which have proved suitable are: hydrocarbons, such as benzene, toluene, xylene, mesitylene, tetrahydronaphthalene, decalin, cyclohexane and higher-boiling ligroin fractions; ethers, such as tetrahydrofuran, dioxane, ethylene glycol dimethyl ether, diethylene glycol dimethyl ether and diphenyl ether; nitriles, such as acetonitrile or propionitrile; ketones, such as ethyl methyl ketone, cyclohexanone and acetone, and dimethylsulfoxide.

In a preferred embodiment of the process according to the invention, the procedure comprises reacting a sulfonamide of the formula II with a chloroformic acid ester of the formula III, or reacting a sulfonyl chloride of the formula IV, in the presence of a base and in an inert solvent at 10° to 80° C., with a urethane; and heating the resulting carbamate of the formula VI together with an amine of the formula VII, in an inert solvent at 80° to 160° C., until the cleavage reaction of alcohol or mercaptan has finished; and isolating the product.

The starting compounds of the formulae II, III, IV, V and VII are known, and can be produced by known methods.

The sulfonylcarbamates of the narrower subformula VIa are novel and were developed specially for carrying out the process according to the invention. They therefore form further subject matter of the present invention.

The novel sulfonylcarbamates correspond to the general formula VIa

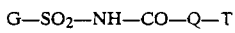   VIa)

wherein

Q is oxygen or sulfur,

T is $C_1$-$C_4$-alkyl, $C_1$-$C_4$-haloalkyl, $C_1$-$C_3$-cyanoalkyl, $C_2$-$C_5$-alkenyl, benzyl, or alkoxyalkyl or alkylthioalkyl having a total of at most 5 carbon atoms G is a radical of the formula

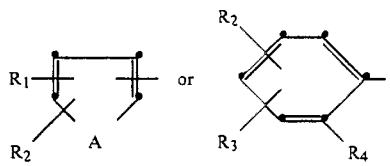

wherein

A is oxygen, sulfur, —$NR_5$—or —C=N—, where $R_5$ is hydrogen, $C_1$-$C_4$-alkyl or —CO—$C_1$-$C_4$-alkyl, $R_1$ is hydrogen, $C_1$-$C_4$-alkyl, halogen, nitro, cyano, —$NH_2$, —$S(O)_n$—$C_1$-$C_4$-alkyl, —$SO_2$—$C_1$-$C_4$-alkoxy, —$SO_2$-di-$C_1$-$C_4$-alkylamino, —CHO, —$CONH_2$, —D—$C_3$-$C_5$-alkynyl, —CO—D—$C_3$-$C_5$-alkynyl, —D—$C_1$-$C_4$alkyl, —D—$C_3$-$C_5$-alkenyl, —CO—$C_1$-$C_4$-alkyl, —CO—D—$C_1$-$C_4$alkyl or —CO—D—$C_3$-$C_5$-alkenyl, n being one or two, and D being an oxygen, sulfur, —NH—or —N($C_1$-$C_4$-alkyl)bridge, $R_2$ is hydrogen, halogen, $CF_3$, $NO_2$, $C_1$-$C_4$alkyl or $C_1$-$C_4$-alkoxy, $R_3$ is hydrogen, fluorine or chlorine, and $R_4$ is halogen, $C_1$-$C_4$-alkyl, nitro, cyano, —$NH_2$, —$S(O)_n$—$C_1$-$C_4$-alkyl, —$SO_2$—$C_1$-$C_4$-alkoxy, —$SO_2$-di-$C_1$-$C_4$-alkylamino, —CHO, —$CONH_2$, —D—$C_3$-$C_5$-alkynyl, —CO-D-$C_3$-$C_5$-alkynyl, trifluoromethyl, or $C_1$-$C_4$-alkoxy substituted by cyano, halogen, $C_1$-$C_4$-alkoxy or $C_1$-$C_4$-alkylthio, or is —D—$C_1$-$C_4$-alkyl, —D—$C_3$-$C_5$-alkenyl, —CO—$C_1$-$C_4$-alkyl, 1,2-dichlorovinyloxy, —CO—D—$C_1$-$C_4$-alkyl or —CO—D—$C_3$-$C_5$-alkenyl, n being 1 or 2, and D being an oxygen, sulfur, —NH—or —N($C_1$-$C_4$-alkyl)bridge, with the proviso that (a) the radical —Q—T is not ethoxy or butyloxy when G is the unsubstituted 2-thienyl radical, (b) the radical —Q—T is not methylthio when G is the 2-tolyl radical, (c) the radical —Q—T is not ethoxy when G is the 2-trifluoromethylphenyl radical or the 2-anisyl radical, and (d) the radical —Q—T is not methoxy when G is the 2-methoxycarbonylphenyl radical or the 2-ethylthiocarbonylphenyl radical.

The Examples which follow serve to further illustrate the invention.

EXAMPLE 1

N-(2-Difluoromethoxyphenyl-sulfonyl)-ethoxycarbamate 1.15 g of 55% sodium hydride are added to a solution of 2.2 g of carbamic acid ethyl ester in 30 ml of ethylene glycol dimethyl ether at 20° to 25° C. The formed suspension is stirred at 20° to 25° C. for 30 minutes; it is then cooled to 10° C. and 6.0 g of 2-difluoromethoxybenzenesulfonyl chloride are added dropwise. The reaction is exothermic, and a slight evolution of gas occurs. After the reaction mixture has been stirred at 20° to 25° C. for one hour, the solvent is evaporated off, and 50 ml of ice-water are added to the residue. The yield after extraction with ethyl acetate, drying, concentration by evaporation of the organic phase and purification of the residue by column-chromatography on silica gel with methylene chloride is 1.7 g (23.3% of theory) of N-(2-difluoromethoxyphenyl-sulfonyl)-ethylcarbamate, m.p. 111°–113° C.

EXAMPLE 2

N-(2-Difluoromethoxyphenyl-sulfonyl)-N'-(4-methoxy-6-methyl-1,3,5-triazin-2-yl)-urea A solution of 1.48 g of N-(2-difluoromethoxy-phenyl-sulfonyl)-ethylcarbamate and 0.62 g of 2-amino-4l-methoxy-6-methyl-1,3,5-triazine in 20 ml of chlorobenzene is refluxed. After concentration of the yellow solution by evaporation, and chromatographical purification of the residue, there is obtained a colourless oil which crystallises from an acetone/diethyl ether mixture by the addition of hexane. The yield is 0.45 g (23.1% of theory) of N-(2-difluoromethoxyphenyl-sulfonyl)-N'-(4-methoxy-6-methyl-1,3,5-triazin-2-yl)-urea, m.p. 140°–141° C.

EXAMPLE 3

N-(2-Chlorophenyl-sulfonyl)-ethyl carbamate 6.65 ml of chloroformic acid ethyl ester are added to a mixture of 12.25 g of 2-chlorophenylsulfonamide, 21.6 g of anhydrous potassium carbamate and 80 ml of anhydrous acetone at 20° to 25° C., and refluxing is carried out for 2 hours. After cooling, the reaction mixture is taken up in 300 ml of ice-water and the mixture is filtered; the pH-value is adjusted to 2 with concentrated hydrochloric acid, and extraction is performed with ethyl acetate. The combined organic phases are washed with water, dried over sodium sulfate and concentrated by evaporation. The yield after crystallisation from an alcohol/water mixture is 14.9 g of N-(2-chlorophenyl-sulfonyl)-ethyl carbamate, m.p. 150°–152° C.

EXAMPLE 4

N-(2-Methoxycarbonylphenyl-sulfonyl)-N'-(4-difluoromethoxy-6-methyl-pyrimidin-2-yl)-urea A solution of 2.73 g of N-(2-methoxycarbonylphenyl-sulfonyl)-methyl carbamate and 1.75 g of 2-amino-4-difluoromethoxy-6-methyl-pyrimidine in 50 ml of absolute dioxane is refluxed for 24 hours. After the solvent has been evaporated off, the residue is dissolved in a 5% sodium carbonate solution, and the solution is filtered; the pH-value is adjusted to 2 by acidifying the concentrated hydrochloric acid, and extraction is performed with ethyl acetate. The combined organic phases are dried over sodium sulfate, and the solvent is evaporated off to thus obtain 3.2 g of N-(2-methoxycarbonyl-phenylsulfonyl)-N'-(4-difluoromethoxy-6-methyl-pyrimidin-2-yl)urea, m.p. 162°–164° C.

The following intermediates of the formula VIa are produced in an analogous manner.

TABLE 1

| Comp. No. | G | —Q—T | Physical data |
|---|---|---|---|
| 1 | 2-Cl—$C_6H_4$— | —$OC_2H_5$ | m.p. 150–152° C. |
| 2 | 2-$OCH_3$—5-$OCH_3$—$C_6H_3$— | —$OC_2H_5$ | m.p. 132–133° C. |
| 3 | 2-$OCH_3$—5-$OCH_3$—$C_6H_3$— | —$SCH_3$ | m.p. 182° C. (decomp.) |
| 4 | 2-$OCHF_2$—$C_6H_4$— | —$OCH_3$ | m.p. 138–140° C. |
| 5 | 2-$OCHF_2$—$C_6H_4$— | —$OC_2H_5$ | m.p. 107–111° C. |
| 6 | 2-$OCHF_2$—$C_6H_4$— | —$OC_4H_9$—n | $n_D^{20}$ = 1.4958 |
| 7 | 2-$OCH_3$—$C_6H_4$— | —$OCH_3$ | |
| 8 | 2-Cl—$C_6H_4$— | —$OCH_3$ | |
| 9 | 2-Cl—$C_6H_4$— | —O—$CH_2$—CH=$CH_2$ | |
| 10 | 2-Cl—$C_6H_4$— | —O—$CH_2$—$C_6H_5$ | |
| 11 | 2-Cl—$C_6H_4$— | —O—$CH_2$—$CF_3$ | |
| 12 | 2-Cl—$C_6H_4$— | —O—$CH_2$—$CCl_3$ | |
| 13 | 2-Cl—$C_6H_4$— | —S—$CH_3$ | |
| 14 | 2-$COOCH_3$—$C_6H_4$— | —$OCH_3$ | m.p. 162–164° C. |
| 15 | 2-$NO_2$—$C_6H_4$— | —$OCH_3$ | |
| 16 | 2-[—O($CH_2$)$_2$—$OCH_3$]—$C_6H_4$— | —$OCH_3$ | |
| 17 | 2-$CF_3$—$C_6H_4$— | —$OCH_3$ | |
| 17 | 2-$CH_3$—$C_6H_4$— | —$OCH_3$ | |
| 19 | (thiophene-COOCH$_3$ structure) | —$OCH_3$ | |
| 20 | 2-$COOCH_3$—$C_6H_4$— | —$OC_2H_5$ | m.p. 73–75° C. |
| 21 | 2-$COOCH_3$—$C_6H_4$— | —$OCH_2$—$CF_3$ | m.p. 106–108° C. |
| 22 | 2-$COOCH_3$—$C_6H_4$— | —$OCH_2$—$C_6H_5$ | m.p. 108° C. |
| 23 | 2-$COOCH_3$—$C_6H_4$— | —$OCH_2$—CH=$CH_2$ | m.p. 51–59° C. |
| 24 | 2-$COOCH_3$—$C_6H_4$— | —$OCH_2CH_2OCH_3$ | $n_D^{21}$: 1,5110 |
| 25 | 2-$COOCH_3$—$C_6H_4$— | —$OC_4H_9$(n) | m.p. 79–82° C. |
| 26 | 2-$COOCH_3$—$C_6H_4$— | —$OCH_2CCl_2$ | $n_D^{21}$: 1,528 |
| 27 | 2-$COOCH_3$—$C_6H_4$— | —$OCH_2CH_2CN$ | m.p. 87°–89° C. |

TABLE 1-continued

| Comp. No. | G | —Q—T | Physical data |
|---|---|---|---|
| 28 | 2-COOCH$_3$—C$_6$H$_4$— | —SCH$_3$ | m.p. 133-4° C. |
| 29 | 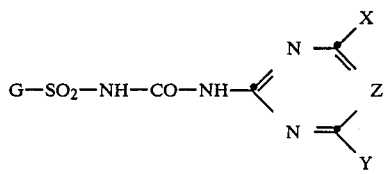 | —OCH$_3$ | |
| 30 | 2-OCH$_2$CH$_2$Cl—C$_6$H$_4$— | —OCH$_3$ | |

What is claimed is:

1. A process for producing a sulfonylurea of the general formula I

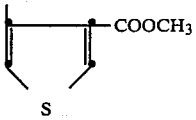 (I)

wherein
Z is an —N= or —CH= radical,
G is a radical of the formula

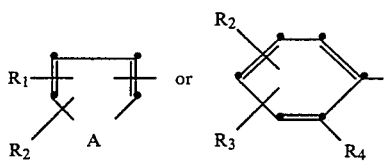

X is C$_1$-C$_4$-alkyl, C$_1$-C$_4$-haloalkyl, C$_1$-C$_4$-alkoxy, C$_1$-C$_4$-alkylthio, halogen, C$_1$-C$_4$-haloalkoxy, C$_1$-C$_4$-alkylamino or di-C$_1$-C$_4$-alkylamino,
Y is C$_1$-C$_4$-alkyl, C$_1$-C$_4$-alkoxy or C$_1$-C$_4$-haloalkoxy,
A is oxygen, sulfur, —NR$_5$— or —C=N—, where R$_5$ is hydrogen, C$_1$-C$_4$-alkyl or —CO—C$_1$-C$_4$alkyl,
R$_1$ is hydrogen, C$_1$-C$_4$-alkyl, halogen, nitro, cyano, —NH$_2$, —S(O)$_n$—C$_1$-C$_4$-alkyl, —SO$_2$—C$_1$-C$_4$-alkoxy, —SO$_2$—di-C$_1$-C$_4$-alkylamino, —CHO, —CONH$_2$, —D—C$_3$-C$_5$-alkynyl, —CO—D—C$_3$-C$_5$-alkynyl, —D—C$_1$-C$_4$-alkyl, —D—C$_3$-C$_5$-alkenyl, —CO—C$_1$-C$_4$-alkyl, —CO—D—C$_1$-C$_4$-alkyl or —CO—D—C$_3$-C$_5$-alkenyl, n being one or two, and D being an oxygen, sulfur, —NH— or —N(C$_1$-C$_4$-alkyl)-bridge,
R$_2$ is hydrogen, halogen, CF$_3$, NO$_2$, C$_1$-C$_4$-alkyl or C$_1$-C$_4$-alkoxy,
R$_3$ is hydrogen, fluorine or chlorine, and
R$_4$ is halogen, C$_1$-C$_4$-alkyl, nitro, cyano, —NH$_2$, —S(O)$_n$—C$_1$-C$_4$-alkyl, —SO$_2$—C$_1$-C$_4$-alkoxy, —SO$_2$-di-C$_1$-C$_4$-alkylamino, —CHO, —CONH$_2$, —D—C$_3$-C$_5$-alkynyl, —CO—D—C$_3$-C$_5$-alkynyl, trifluoromethyl, or C$_1$-C$_4$-alkoxy substituted by cyano, halogen, C$_1$-C$_4$-alkoxy or C$_1$-C$_4$-alkylthio, or is —D—C$_1$-C$_4$-alkyl, —D—C$_3$-C$_5$-alkenyl, —CO—C$_1$-C$_4$-alkyl, 1,2-dichlorovinyloxy, —CO—D—C$_1$-C$_4$-alkyl or —CO—D—C$_3$-C$_5$-alkenyl, n being one or two, and D being an oxygen, sulfur, —NH— or —N(C$_1$-C$_4$-alkyl)-bridge, which process comprises reacting a sulfonamide of the formula II

G—SO$_2$—NH$_2$ (II), in the presence of a base, with a chloroformic acid ester of the formula III Cl—CO—Q—T (III), or a sulfonyl chloride of the formula IV G—SO$_2$—Cl (IV), in the presence of a base, with a urethane of the formula V

H$_2$N—CO—Q—T (V), wherein G has the meaning defined under the formula I, Q is oxygen or sulfur, and
T is C$_1$-C$_4$-alkyl, benzyl, C$_1$-C$_4$-haloalkyl, C$_1$-C$_3$-cyanoalkyl, C$_2$-C$_5$-alkenyl, or alkoxyalkyl or alkylthioalkyl having a total of at most 5 carbon atoms; and converting the formed carbamate of the formula VI

G—SO$_2$—NH—CO—Q—T (VI)

by reaction with an amine of the formula VII

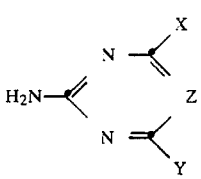 (VII)

wherein G, Q, T, X, Y and Z have the meanings defined in the foregoing, into the sulfonylurea of the formula I.

2. A process according to claim 1, wherein the reaction of the carbamate of the formula VI with the amine of the formula VII is performed at a temperature of 50°-220° C.

3. A process according to claim 2, wherein the reaction temperature is 80° to 160° C.

4. A process according to claim 1, wherein the reaction of the carbamate of the formula VI with the amine of the formula VII is performed in an inert solvent.

5. A process according to claim 4, wherein the solvent is selected from the group comprising: hydrocarbons, ethers, nitriles, ketones or dimethyl sulfoxide.

6. A process according to claim 1, wherein the reaction of the sulfonamide of the formula II with the chloroformic acid ester of the formula III, or of the sulfonyl chloride of the formula IV with the urethane of the formula V is performed at 0° to 140° C.

7. A process according to claim 6, wherein the reaction temperature is 10° to 80° C.

8. A process according to claim 1, wherein the reaction of the sulfonamide of the formula II with the chloroformic acid ester of the formula III, or of the sulfonyl chloride of the formula IV with the urethane of the formula V is performed in the presence of a base from the group comprising: carbonates, hydrogen carbonates, oxides and tertiary amines.

9. A process according to claim 1, wherein the reaction of the sulfonamide of the formula II with the chloroformic acid ester of the formula III, or of the sulfonyl chloride of the formula IV with the urethane of the formula V is performed in an inert solvent.

10. A process according to claim 9, wherein the solvent is selected from the group comprising: hydrocarbons, ethers, nitriles, ketones or dimethyl sulfoxide.

11. A process according to claim 1, which process comprises reacting a sulfonamide of the formula II with a chloroformic acid ester of the formula III, or reacting a sulfonyl chloride of the formula IV, in the presence of a base and in an inert solvent at 10° to 80° C., with a urethane of the formula V, and heating the resulting carbamate of the formula VI together with an amine of the formula VII, in an inert solvent at 80° to 160° C., until the cleavage reaction of alcohol or mercaptan has finished; and isolating the product.

* * * * *